United States Patent [19]

Ernst

[11] 4,262,525

[45] Apr. 21, 1981

[54] HARDNESS TESTING APPARATUS PROVIDED WITH A SAFETY STOP DEVICE

[76] Inventor: Alfred Ernst, Via San Martino, 6, Vezia Ticino, Switzerland

[21] Appl. No.: 101,749

[22] Filed: Dec. 6, 1979

[30] Foreign Application Priority Data

Dec. 15, 1978 [CH] Switzerland ............... 12805/78

[51] Int. Cl.³ .............................................. G01N 3/44
[52] U.S. Cl. ..................................................... 73/81
[58] Field of Search ....................................... 73/81, 83

[56] References Cited

U.S. PATENT DOCUMENTS 3,590,630  6/1971  Ericksson ............................... 73/83

Primary Examiner—Gerald Goldberg
Assistant Examiner—Joseph W. Roskos
Attorney, Agent, or Firm—Michael J. Striker

[57] ABSTRACT

The invention refers to a hardness testing apparatus operating under great applied loads, for example up to 3,000 Kg. provided with a safety stop device preventing the main load application and/or returns the instrument to a rest position, when the workpiece to be tested is not exactly disposed under the reference plane in order not to be touched by the indentor, or when under the instrument an operator's hand is inserted accidentally.

3 Claims, 1 Drawing Figure

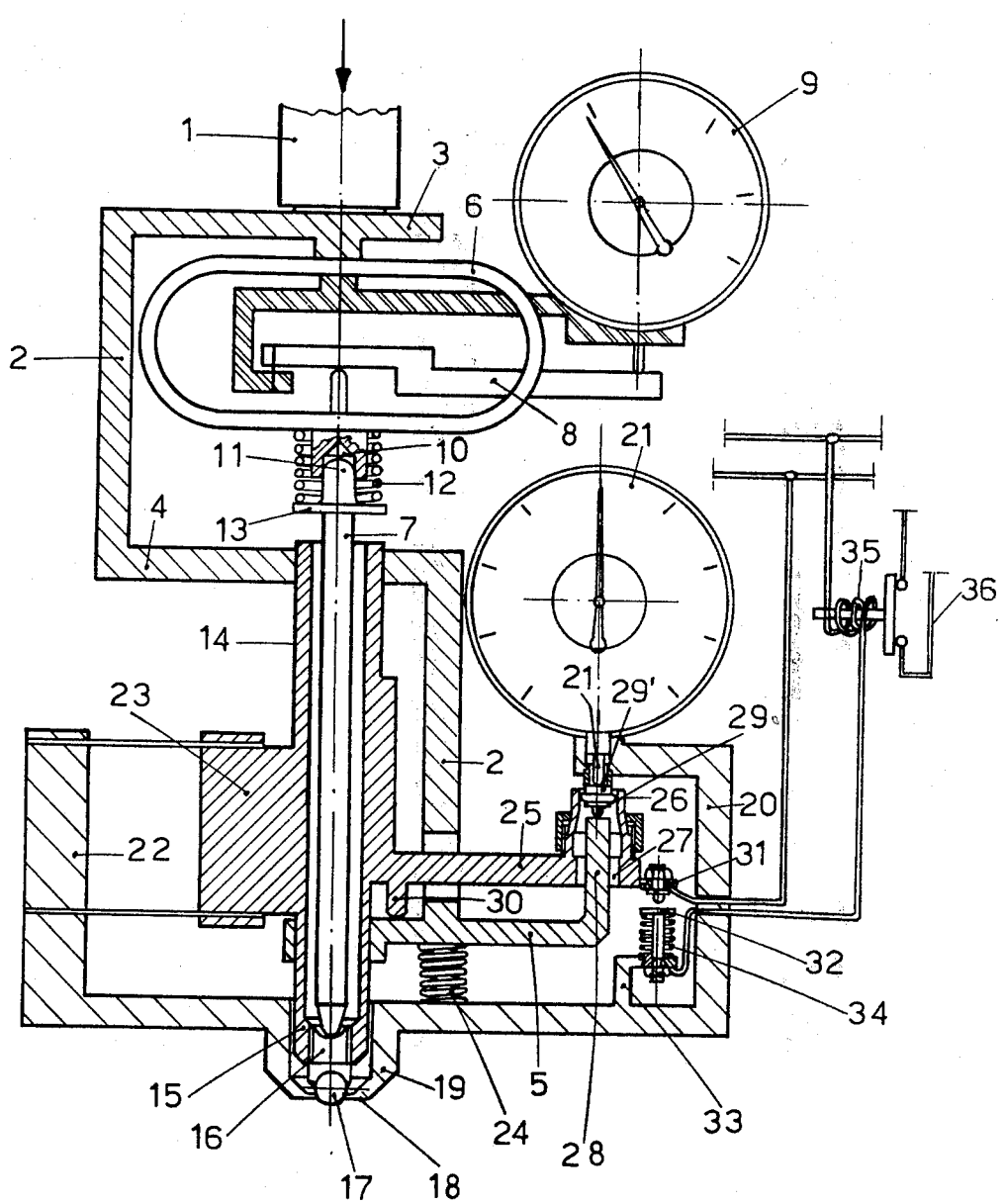

HARDNESS TESTING APPARATUS PROVIDED WITH A SAFETY STOP DEVICE

BACKGROUND OF THE INVENTION

The present invention relates to a hardness testing apparatus operating with a preload and a main load or metering load, wherein the indentor moves relative to a reference plane, which normally abuts on the workpiece to be tested, said hardness testing apparatus being provided with a safety stop device.

Hardness testing apparatuses, acting with a preload and a main load are known and they operate with a very high applied load, for example up to 3.000 Kg, wherein the applied load is transmitted by a thrust member apt to furnish a thrust, coaxial or parallel to the indentor axis, for example the rod of an hydraulic jack.

Because of the high applied load, the operation of said hardness testing apparatuses may become dangerous in some cases, such as a failed truing of the workpiece to be tested or a great inclination of the same workpiece, so that the indentor tip projects more than the usual rate beyond the reference plane, causing failures to the members stressed by the main load.

Another dangerous case is when the apparatus can harm the workers, for example in case of a careless insertion of a hand between the indentor and the workpiece to be tested.

Devices able to verify the penetrating rate of the indentor are already known in the prior art, but they are designed to ascertain if the workpiece hardness is within the required limits.

The need to test the real hardness of the workpiece through the preload and main load system, has always required the application of the main load, so that said known devices are not employable as safety devices able to prevent the application of the main load, in the event that a hand is interposed between the workpiece to be tested and the indentor, or in the event that the workpiece to be tested does not interfere with the indentor while interferring with the reference plane.

Examples of said known devices are set forth in U.S. Pat. No. 2,858,696 and U.K. Pat. No. 1,245,295.

U.K. Pat. No. 1,183,277 teaches a safety device for a manually controlled instrument able to signal that the testing cycle must be stopped when the preload is disturbed by the anticipated application of the main load. In any case, however, the stop of the cycle takes place only after the main load has been applied.

U.S. Pat. No. 4,059,990 teaches a hardness testing apparatus that seems to operate with a high main load, as the indentor is moved by a double-acting cylinder.

A control fluid flow, such as air, is more or less throttled proportionally to the workpiece hardness and a gauge responsive to this throttling causes the starting of an alarm or the ejection of the workpiece being tested, when the hardness amount is out of the predetermined limits.

Even in this case, however, the device operates when the main load has been applied.

The U.S. Pat. No. 3,934,463 teaches a hardness testing apparatus which does not operate according to the preload and main load system, but it operates in such a way that the indentor penetrates into the workpiece at a predetermined rate and the hardness is tested with reference to the load which has been applied on the indentor. Even in this event, a dangerous applied load acts on the indentor and on the reference plane.

SUMMARY OF THE INVENTION

One object of the present invention is to eliminate all dangers of injury by interrupting the testing operation before the application of the main load, in the event that in the preloading step the indentor moves beyond the reference plane at a rate higher than the maximum penetration predetermined for the indentor under the same main load, in reference to materials to be tested, such as metals.

In this way, when the indentor does not touch the surface of the workpiece to be tested, even if it abuts on the latter with the reference plane, or when the indentor penetrates into an underlying soft body (such as a hand) at a rate greater than the maximum penetration foreseen under the main load, the main load application is prevented and the upward return of the instrument is caused, avoiding dangerous consequences.

The present invention relates to a hardness testing apparatus operating with a preload and a main load, wherein the indentor moves relative to a reference plane which normally abuts on the surface of the workpiece to be tested and wherein the approaching operations of the indentor toward the workpiece and the preload and the main load applications are executed automatically by means of a thrust member. According to the invention there is provided a member able to send a signal to stop the testing cycle at any moment before the main load application to prevent the application of the foreseen whole load (preload and main load), when the indentor does not meet any appreciable resistance, as in the case of a hand accidentally inserted under the indentor, or because of an anomalous position of the workpiece to be tested, so that the indentor moves beyond the reference plane at a rate greater than the maximum projection foreseen in the normal operation.

The element issuing the signal that stops the thrust member is constituted by a pair of electric contacts, the first one disposed on an element movable with the indentor and the other one, disposed on an element movable with the reference plane, said contacts, at rest, being spaced from one another in order to get in touch only when the indentor moves beyond the reference plane at a rate greater than the maximum projection foreseen in the normal operation.

BRIEF DESCRIPTION OF THE DRAWING

The object of the present invention, by way of a not limitative exemplary embodiment, is shown in the sole FIGURE of the enclosed drawing, showing a diagrammatical preload and load hardness testing apparatus in a rest position.

DESCRIPTION OF PREFERRED EMBODIMENTS

Referring to the FIGURE, reference 1 indicates the end portion of a thrust member able to support and move the hardness testing apparatus and to furnish the applied load thereto.

Said thrust member, for example, can be the rod of a double-acting hydraulic jack, whose up and down movements are controlled by a solenoid valve.

A rigid frame 2 is fixed to the thrust member 1, said rigid frame being provided with an upper horizontal arm 3, an intermediate horizontal arm 4, and a lower horizontal arm 5. Under the horizontal arm 3, a load cell 6 is disposed, constituted by a metallic resilient ring, said load cell 6 being able to transmit the main load to the indentor rod 7, in a way to be explained.

The vertical deformation of the load cell 6 is sensed by a lever 8, whose displacement operates a gauge 9 the function of which is to stop the displacement of the member 1 when the deformation of the cell 6 corresponds to the desired main load, for example 3.000 Kg.

Under the load cell 6 there is provided a seat 10 receiving with a certain play the upper end 11 of the indentor rod 7. A spring 12 is disposed around said seat, pressed between the load cell 6 and a flange 13 provided on the rod 7. The spring 12 is the spring designed to furnish the preload to the indentor, said preload being several times lower than the main load.

The horizontal arms 4 and 5 of frame 2 have two coaxial holes and a tubular member 14 guided therein, rod 7 being disposed inside member 7.

The lower end 15 of the tubular member 14 acts as a guide for the indentor-carrier 16, the indentor being in this case formed by a ball 17.

The reference plane 18, is furnished by a bushing 19 which on one side is prolonged at 20 to form the support for the metering gauge 21, and, on the other side, if extended at 22 to form a guiding coupling with the tubular member 14, in this event the coupling being embodied by two parallel resilient laminae engaged to the element 22 and, on the other side, to a lateral projection 23 of the member 14.

A coil spring 24 of a relatively low load, for example 7/8 Kg., is interposed between the reference plane and the rigid frame 2, such as to secure the steady bearing of the reference plane 18 on the workpiece to be tested.

The tubular element 14 continues on one side with an arm 25 ending with an upwardly directed fork 26 whose arms are disposed around a hole 27 provided on the same arm 25.

The hole 27 is traversed by the upwardly directed end 28 of the arm 5 and, in rest position, said end touches a follower 29 of a slider 29' of a unit normally employed for automatic zero setting.

A stop 30 depending on the arm 25 of the tubular member 14 interferes with the arm 5 of the rigid frame 2, reducing the relative downwardly displacement of the tubular member 14.

In accordance with the present invention, a first electric contact 31 is disposed at the end of the arm 25, while a second electric contact 32, preferably axially sprung by a spring 34, is disposed on a support 33, provided on the frame of the reference plane 18. The two contacts 31 and 32 in preload position, that is, in the position wherein under the preload the indentor 17 is induced to retract relative to the reference plane, are spaced from one another at a distance a bit greater than the maximum penetration foreseen for the indentor when the latter acts on a normal workpiece to be tested.

The indentor projection, at rest, is less than the maximum foreseen projection, as it is limited by the stop 30.

Said arrangement assures that, until the indentor 17 operates on some predetermined materials and effectively acts thereon, the two contacts will not be induced to get in touch.

Contacts 31 and 32 are inserted in the electric circuit of an appropriate member, for example the coil 35 of a relay which, when its coil is energized, attracts an armature which interrupts a second electrical circuit 36. Said circuit 36 acts on the thrust power member, by stopping it and preferably by causing the upward movement of the instrument. For example, it can act on the solenoid valve controlling the double-acting cylinder which moves the member 1, by feeding the return chamber of said cylinder.

The normal operation of said apparatus takes place in the following way. The descent of member 1 is caused, so that it lowers the apparatus until the indentor 17 meets the workpiece to be tested and then it retracts relative to the reference plane 18, until the latter does not touch the workpiece to be tested. At this moment, the spring 12 is compressed and it furnishes the preload.

The reference plane presses on the workpiece with a limited pressure provided by the spring 24. At this point the end of the raised portion 28 detaches from the slider 29' which, by friction of the fork 26, follows the movement of the indentor.

As the member 1 continues its descent with frame 2, the rod 11 touches the bottom of the seat 10, so that through the load cell 6 the main load is transmitted to the indentor, said main load being sensed by the gauge 9 through the lever 8. When gauge 9 reaches a certain level, it stops by electric means the descent of member 1, keeping the main load rate constant.

The main load having been applied, the indentor 17 penetrates into the workpiece. In this way the friction fork 26 can follow the displacement of the indentor dragging a slider 29'. The follower 21 of the gauge follows the slider 29' and allows the gauge to indicate the penetration rate under the main load.

In case wherein there is an empty space caused under the reference plane by a missed truing of the workpiece or by a great inclination of the latter, or in a case wherein there is a soft body, such as a hand, under the reference plane during the preload step, the spring 12 is sufficient to thrust the indentor outwardly from the reference plane at a rate that is greater than the rate foreseen for a normal testing. Said preload spring 12, which, for an applied load of 3.000 Kg., has its own load (about 40 to 100 Kg.), stops the indentor reascent, but the reference plane goes up, overcoming the force of the spring 24, the amount of said force being of about 7 Kg.

When the indentor projects beyond the operating rate, contacts 31 and 32 get in touch, causing the energization of relay 35, which in turn changes the condition of the electrical circuit 36, which immediately provides to stop the further descent of the member 1 and to cause its upward return together with the instrument.

For example, when operating with a main load of 3,000 Kg and a spheric indentor having a diameter of 10 mm, the safety projection of the indentor relative to the reference plane, sufficient to cause the touching of the two contacts 31 and 32, can be predetermined at about 1 mm, as the projection reached by the indentor during the normal operation with iron materials (such as steel, cast iron) is less than a millimeter.

The invention, of course, is valid for any value of the main load even though it is less than 3,000 Kg.

I claim:
1. Hardness testing apparatus operating with a preload and a main load, wherein an indentor moves relative to a reference plane which normally abuts on the surface of the workpiece to be tested, and wherein the approaching operations of the indentor to the workpiece and the preload and main load applications are executed automatically by means of a thrust member, comprising a member able to send a signal to stop the testing cycle at any moment before the main load appli- cation, to prevent the application of the foreseen whole load composed of the preload and main load, when the indentor fails to meet any appreciable resistance, as in the case of a hand accidentally inserted by the operator under the indentor, or because of an anomalous position of the workpiece to be tested, so that the indentor projects beyond the reference plane at a rate greater than the maximum projection foreseen in normal operation.

2. Hardness testing apparatus according to claim 1, wherein the member issuing the signal which stops the thrust member, is constituted by a pair of electric contacts, the first one disposed on an element movable with the indentor and the other one disposed on an element movable with the reference plane, such contacts being spaced therebetween, in order to get in touch only when the indentor projects beyond the reference plane at a rate greater than maximum projection foreseen in the normal operation.

3. Hardness testing apparatus according to claims 1 or 2, wherein the member issuing the signal which stops the testing cycle, also causes the inversion of the thrust member to reset the testing instrument to a rest position.

* * * * *